US011369282B1

(12) United States Patent
Jiang et al.

(10) Patent No.: US 11,369,282 B1
(45) Date of Patent: Jun. 28, 2022

(54) METHOD FOR GENERATING TRANSCRANIAL MAGNETIC STIMULATION (TMS) COIL POSE ATLAS BASED ON ELECTROMAGNETIC SIMULATING CALCULATION

(71) Applicant: INSTITUTE OF AUTOMATION, CHINESE ACADEMY OF SCIENCES, Beijing (CN)

(72) Inventors: Tianzi Jiang, Beijing (CN); Gangliang Zhong, Beijing (CN); Zhengyi Yang, Beijing (CN); Liang Ma, Beijing (CN)

(73) Assignee: INSTITUTE OF AUTOMATION, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/539,150

(22) Filed: Nov. 30, 2021

(30) Foreign Application Priority Data

Jan. 14, 2021 (CN) .......................... 202110048839.2

(51) Int. Cl.
*A61B 5/055* (2006.01)
*A61B 5/00* (2006.01)
(Continued)

(52) U.S. Cl.
CPC ............ *A61B 5/055* (2013.01); *A61B 5/4064* (2013.01); *A61B 34/10* (2016.02); *A61N 2/006* (2013.01); *A61N 2/02* (2013.01)

(58) Field of Classification Search
CPC ....... A61B 5/055; A61B 5/4064; A61B 34/10; A61N 2/006; A61N 2/02
See application file for complete search history.

(56) References Cited

U.S. PATENT DOCUMENTS

| 2004/0078056 A1 | 4/2004 | Zangen et al. |
| 2016/0001092 A1 | 1/2016 | Solehmainen |

(Continued)

FOREIGN PATENT DOCUMENTS

| CN | 101516444 A | 8/2009 |
| CN | 102814001 A | 12/2012 |

(Continued)

OTHER PUBLICATIONS

Zhou Tianpeng, et al., Research Progress of Positioning Method of Transcranial Magnetic Stimulation, Chinese Journal of Biomedical Engineering, 2017, pp. 741-748, vol. 36, No. 6.
(Continued)

*Primary Examiner* — Hien N Nguyen
(74) *Attorney, Agent, or Firm* — Bayramoglu Law Offices LLC

(57) ABSTRACT

A method for generating a transcranial magnetic stimulation (TMS) coil pose atlas based on electromagnetic simulating calculation includes: constructing coil array positions and orientations of a scalp in a standard Montreal Neurological Institute (MNI) space and matching the coil array positions and orientations of the scalp to a brain space of an individual to obtain coil array positions and orientations of the brain space of the individual; using a finite element calculation method to simulate the coil array positions of the brain space of the individual to obtain induced electric field distributions of brain tissue in different coil orientations; obtaining optimal regulation effects based on the induced electric field distributions of the brain tissue; and obtaining a coil position and orientation corresponding to each optimal regulation effect as an optimal coil pose of each divided brain area of the individual, and constructing a TMS coil pose atlas of the individual.

9 Claims, 7 Drawing Sheets

(51) Int. Cl.
*A61B 34/10* (2016.01)
*A61N 2/02* (2006.01)
*A61N 2/00* (2006.01)

(56) References Cited

U.S. PATENT DOCUMENTS

| | | | |
|---|---|---|---|
| 2017/0045601 A1* | 2/2017 | Akhtari | A61B 5/0042 |
| 2017/0049387 A1 | 2/2017 | Saitoh et al. | |
| 2018/0271397 A1* | 9/2018 | Montgomery | G06T 7/0012 |
| 2019/0320966 A1 | 10/2019 | Zhu | |

FOREIGN PATENT DOCUMENTS

| | | |
|---|---|---|
| CN | 102908145 A | 2/2013 |
| CN | 104123416 A | 10/2014 |
| CN | 105572488 A | 5/2016 |
| CN | 107519579 A | 12/2017 |
| EP | 2684518 A1 | 1/2014 |
| WO | 2018183887 A1 | 10/2018 |

OTHER PUBLICATIONS

Nie Wen-Liang, et al., Simulation and Research in Transcranial Magnetic Stimulation Based on Three Dimensional Finite Element, Journal of Chengdu University of Information Technology, 2012, pp. 349-353, vol. 27, No. 4.

* cited by examiner

METHOD FOR GENERATING TRANSCRANIAL MAGNETIC STIMULATION (TMS) COIL POSE ATLAS BASED ON ELECTROMAGNETIC SIMULATING CALCULATION

CROSS REFERENCE TO THE RELATED APPLICATIONS

This application is based upon and claims priority to Chinese Patent Applications No. 202110048839.2, filed on Jan. 14, 2021, the entire contents of which are incorporated herein by reference.

TECHNICAL FIELD

The present invention belongs to the technical field of cognitive neuroscience, and more particularly, relates to a method, system, and device for generating a transcranial magnetic stimulation (TMS) coil pose atlas based on electromagnetic simulating calculation.

BACKGROUND

A brain atlas is an important means to study the structure and function of a brain, and provides a new perspective and research method for an accurate new-generation TMS neuromodulation technology. At present, TMS mainly uses traditional anatomical brain atlases to guide the positioning of TMS coils. Most of these atlases are drawn based on cadaver specimens, only contain information about local areas, and lack description of functional subregions. This leads to limited clinical effects, and it is difficult to implement the accurate positioning of a target area of TMS neuromodulation in a spatial dimension. In addition, a position and a scope of a brain area regulated by TMS are mainly affected by the positioning of the TMS coil and an instantaneous induced electric field in brain tissue. However, a difference in an electrical conductivity parameter of the brain tissue can cause a specific offset such that the brain area to be effectively regulated by TMS is not below the center of the coil. In clinical or scientific research experiments, directly placing the coil at a position of the scalp corresponding to the target area cannot effectively and accurately regulate the target brain area. Therefore, positioning the TMS coil based on a regular brain atlas cannot effectively regulate the target area. The key to accurately regulating the target area by TMS is to construct a TMS coil pose atlas based on a fine and accurate brain atlas and a real induced electric field calculation model.

A human brainnetome atlas uses a multi-modal magnetic resonance imaging technology to non-invasively divide the structure and functional areas of the human brain, and has finer brain area division, different subregion anatomy, and functional connection modes than the existing brain atlas. Therefore, by determining the TMS regulation target area based on the human brainnetome atlas, fine information such as a pose and neural circuit of the target area can be obtained for regulation. After accurate spatial positioning of the target area is obtained based on the human brainnetome atlas, the TMS regulation effect is still required to determine the effective coil positioning. Benefiting from the development of brain imaging technology, image processing algorithms, and numerical calculation methods, an electromagnetic simulating calculation method of TMS provides an effective way to study accurate TMS induced electric field distributions. However, the TMS simulating calculation method requires theoretical knowledge and a large amount of calculation, resulting in that researchers still cannot determine the coil position easily and quickly. In addition, it is difficult to use an existing method to obtain a correspondence between the TMS coil position and the TMS regulation effect.

The TMS coil pose atlas constructed based on the brainnetome atlas can provide a standard coil positioning platform to facilitate the obtaining of coil positioning corresponding to different target regulation areas and optimal regulation effects. However, the existing method cannot provide a TMS coil positioning solution based on an area division result in the accurate brain atlas and regulation effects. Therefore, constructing the TMS coil pose atlas based on the human brainnetome atlas is still one of the biggest challenges of the TMS technology.

SUMMARY

To resolve the foregoing problem that fast and accurate positioning of an existing TMS coil cannot be implemented based on electromagnetic regulation effect in the prior art, a first aspect of the present invention provides a method for generating a TMS coil pose atlas based on electromagnetic simulating calculation, including the following steps:

step S10: constructing coil array positions and orientations of a scalp in a standard Montreal Neurological Institute (MNI) space and matching the coil array positions and orientations of the scalp to a brain space of an individual to obtain coil array positions and orientations of the brain space of the individual;

step S20: constructing a finite element model for the electromagnetic simulating calculation based on obtained structural magnetic resonance images and diffusion tensor magnetic resonance images of a brain of the individual, using a finite element calculation method to simulate positioning of a TMS coil at the coil array positions of the brain space of the individual to obtain induced electric field distributions of brain tissue in different coil orientations;

step S30: registering a brainnetome atlas of the standard space to the brain space of the individual to obtain a brain area division result of the individual, and obtaining a first electric field intensity and a second electric field intensity based on the induced electric field distributions of the brain tissue; and using a maximum value of a sum of the first electric field intensity and a ratio of the first electric field intensity to the second electric field intensity as an optimal regulation effect, where the first electric field intensity is an average electric field intensity of a region of interest (ROI), the second electric field intensity is an average electric field intensity of a region other than the ROI in each divided brain area, namely, an electric field intensity of a non-ROI, and the ROI is a spherical region with a specified radius around a center of each divided brain area of the individual; and step S40: obtaining a coil position and orientation corresponding to each optimal regulation effect as an optimal coil pose of each divided brain area of the individual; and constructing a TMS coil pose atlas of the individual based on the optimal coil pose.

In some preferred implementations, the step of constructing the coil array positions of the scalp in the standard MNI space may specifically include:

step S11: marking anatomical reference points of the scalp in the standard MNI space, where the anatomical reference points include a nasion Nz, an occipital protuberance Iz, a front vertex of a right external pinna APR, and a front vertex of a left external pinna APL;

step S12: obtaining a curve l1 for connecting Nz and Iz and a curve l2 for connecting APR and APL, determining an intersection point of l1 and l2 as a central point Cz, and projecting Cz onto a plane on which Nz and APR are located to obtain a point O; and establishing an equiangular coordinate system based on O, Cz, Nz, and APR, where O is an origin of the coordinate system, Nz is in a positive orientation of an x-axis of the coordinate system, APR is in a positive orientation of a y-axis of the coordinate system, and Cz is in a positive orientation of a z-axis of the coordinate system;

step S13: connecting Nz, Cz, Iz, and O sequentially, dividing an Nz-O-Iz angle into M equal angles α, and determining a point at which a radial line in each orientation intersects the scalp as p(i), where p(1) represents Nz, p(M+1) represents Iz, and M is a positive integer; and step S14: for each point p(i), connecting APL, p(i), APR, and O sequentially, dividing an included angle into M equal angles θ, and determining a point at which a radial line in each orientation intersects the scalp to be p(i, j) as a coil array position of the scalp in the standard MNI space, where p(i, 1) represents APL, and p(i, M+1) represents APR.

In some preferred implementations, a method for constructing the coil array orientations of the scalp in the standard MNI space may specifically include:

determining a normal vector and tangent plane of a coil array pose of the scalp in the standard MNI space; and defining a posterior-to-anterior (PA) orientation on a sagittal plane in a medical imaging space as a 0-degree orientation, and translating the 0-degree orientation to a specific coil array position to locate the 0-degree orientation of the position, where a PA orientation with the position as an origin and toward the sagittal plane is expressed as PA0, and angles of other orientations on the coil tangent plane are set based on PA0.

In some preferred implementations, a method for obtaining the induced electric field distributions of the brain tissue in different coil orientations in step S20 may specifically include:

obtaining an electrical conductivity parameter of each brain tissue of the brain space of the individual based on the structural magnetic resonance images, dividing the brain space into N parts based on a threshold of the electrical conductivity parameter, and performing three-dimensional reconstruction to obtain a finite element geometric model;

calculating a diffusion tensor matrix and an eigenvalue and an eigenvector of the diffusion tensor matrix based on the diffusion tensor magnetic resonance images; and constructing an anisotropic electrical parameter of the brain tissue based on an inference that an eigenvalue of an electrical conductivity tensor matrix of a volume constraint model is proportional to an eigenvalue of the diffusion tensor matrix, and an eigenvector of the electrical conductivity tensor matrix is identical to an eigenvector of the diffusion tensor matrix; and constructing the finite element model for the electromagnetic simulating calculation of the individual based on the finite element geometric model and the anisotropic electrical parameter of the brain tissue, and using the finite element calculation method to simulate the positioning of the TMS coil at the coil array positions of the brain space of the individual to obtain the induced electric field distributions of the brain tissue in different coil orientations.

In some preferred implementations, the volume constraint model may be as follows:

$$\frac{4}{3}\pi(\sigma_{iso})^3 = \frac{4}{3}\pi(\sigma_1\sigma_2 \ldots \sigma_i)$$

where $\sigma_{iso}$ represents an isotropic electrical conductivity parameter of the brain tissue, and $\sigma_i$ represents the eigenvalue of the electrical conductivity tensor matrix.

In some preferred implementations, the optimal regulation effect may be calculated by using the following formulas:

$$EF_{max}(i) = \max_{k \times m \in [s]} |EF(P_{k(i)}, O_{m(i)})|$$

$$EF(i) = E_{ROI(i)} + \frac{E_{ROI(i)}}{E_{non-ROI(n \in Tc)}}$$

where EF(i) represents a regulation effect, namely, an induced electric field intensity, $EF_{max}(i)$ represents the optimal regulation effect, $E_{ROI(i)}$ represents an average induced electric field intensity of an $i^{th}$ ROI, $E_{non-ROI(n \in Tc)}$ represents an average induced electric field intensity of a region other than the $i^{th}$ ROI in a current divided brain area, $P_{k(i)}$ represents a coil position corresponding to the $i^{th}$ ROI, $O_{m(i)}$ represents a coil orientation corresponding to the $i^{th}$ ROI, k represents a number of coil positions, and m represents a number of coil orientations.

A second aspect of the present invention provides a system for generating a TMS coil pose atlas based on electromagnetic simulating calculation, including an array pose acquisition module, a finite element simulating calculation module, an optimal regulation effect acquisition module, and a pose atlas construction module.

The array pose acquisition module is configured to construct coil array positions and orientations of a scalp in a standard MNI space and match the coil array positions and orientations of the scalp to a brain space of an individual to obtain coil array positions and orientations of the brain space of the individual.

The finite element simulating calculation module is configured to construct a finite element model for the electromagnetic simulating calculation based on obtained structural magnetic resonance images and diffusion tensor magnetic resonance images of a brain of the individual, use a finite element calculation method to simulate the coil array positions of the brain space of the individual to obtain induced electric field distributions of brain tissue in different coil orientations.

The optimal regulation effect acquisition module is configured to register a brainnetome atlas of the standard space to the brain space of the individual to obtain a brain area division result of the individual, and obtain a first electric field intensity and a second electric field intensity based on the induced electric field distributions of the brain tissue; and use a maximum value of a sum of the first electric field intensity and a ratio of the first electric field intensity to the second electric field intensity as an optimal regulation effect. The first electric field intensity is an average electric field intensity of an ROI. The second electric field intensity is an average electric field intensity of a region other than the ROI in each divided brain area, namely, an electric field intensity of a non-ROI. The ROI is a spherical region with a specified radius around a center of each divided brain area of the individual.

The pose atlas construction module is configured to obtain a coil position and orientation corresponding to each optimal regulation effect as an optimal coil pose of each divided brain area of the individual; and construct a TMS coil pose atlas of the individual based on the optimal coil pose.

A third aspect of the present invention provides a device, including at least one processor and a memory communicatively connected to the at least one processor. The memory stores an instruction executable by the processor. The instruction is configured to be executed by the processor to implement the foregoing method for generating a TMS coil pose atlas based on electromagnetic simulating calculation.

A fourth aspect of the present invention provides a computer-readable storage medium. The computer-readable storage medium stores a computer instruction. The computer instruction is configured to be executed by a computer to implement the foregoing method for generating a TMS coil pose atlas based on electromagnetic simulating calculation.

The present invention has the following beneficial effects:

The present invention implements fast and accurate positioning of the TMS coil. In the present invention, the coil array positions and orientations of the scalp in the standard MNI space are constructed by using an equiangular division method. This can accurately describe placement space of the coil and ensure repeatability among different individuals. In addition, in combination with the magnetic resonance images, the brainnetome atlas, and the finite element model, a correspondence between the regulation effect and the coil pose is calculated, the TMS coil pose atlas is constructed, and an optimal coil pose corresponding to a target area is directly obtained. This implements fast and accurate positioning of the TMS coil and can effectively resolve the coil positioning problem in non-invasive TMS neuromodulation.

BRIEF DESCRIPTION OF THE DRAWINGS

Other features, objectives, and advantages of the present invention will become more apparent upon reading the detailed description of the non-restrictive embodiments made below with reference to the accompanying drawings.

DETAILED DESCRIPTION OF THE EMBODIMENTS

To make the objectives, technical solutions, and advantages of the present invention clearer, the technical solutions in the embodiments of the present invention are described clearly and completely below with reference to the accompanying drawings. Apparently, the described embodiments are some rather than all of the embodiments. All other embodiments obtained by a person of ordinary skill in the art based on the embodiments of the present invention without creative efforts shall fall within the protection scope of the present invention.

The present invention is further described in detail below with reference to the accompanying drawings and specific embodiments. It should be understood that the specific embodiments described herein are merely intended to explain the present invention, rather than to limit the present invention. It should also be noted that, for ease of description, only the parts related to the present invention are shown in the accompanying drawings.

It should be noted that the embodiments in the present invention and features in the embodiments may be combined with each other if no conflict occurs.

Figure 1:
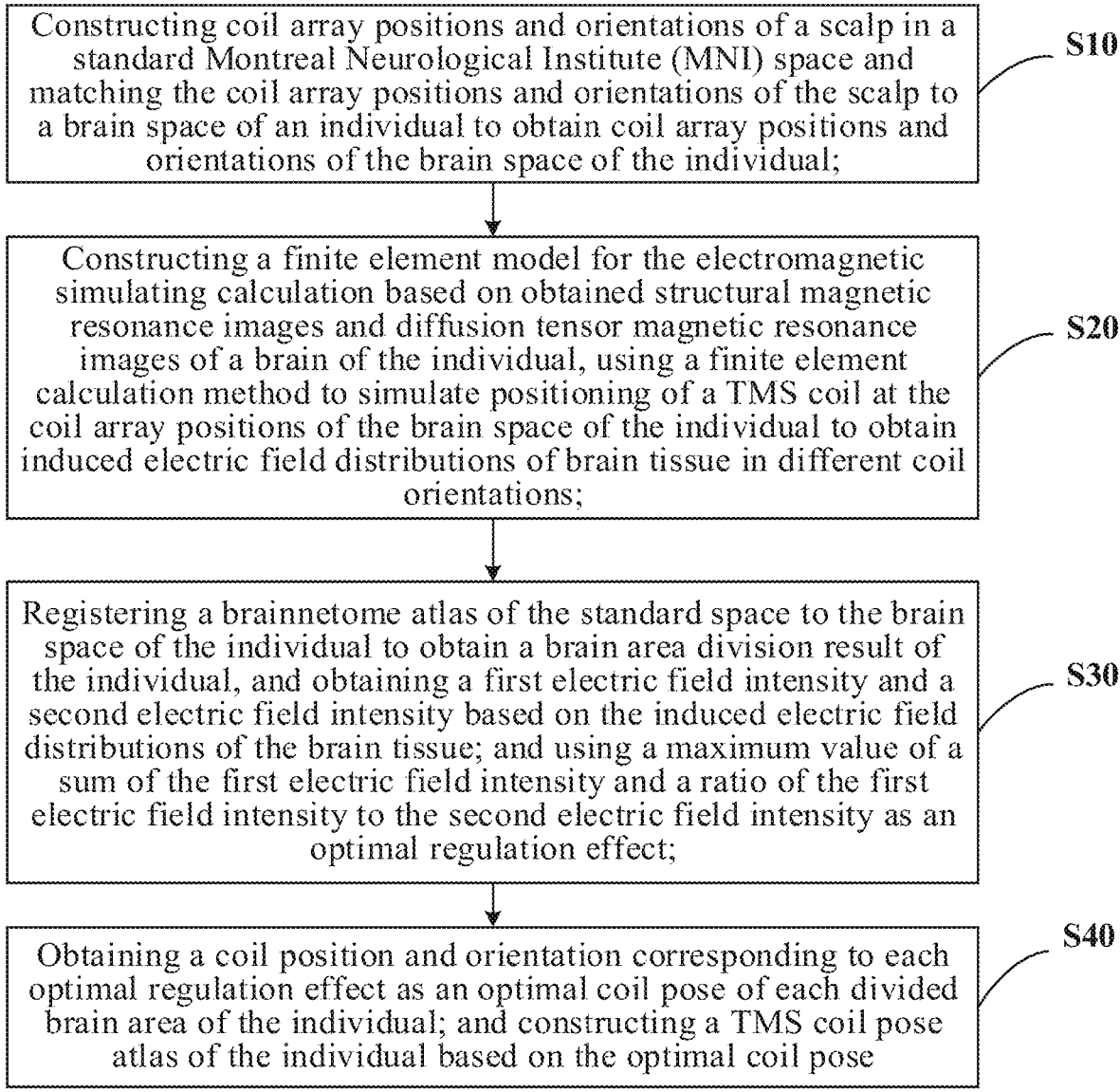
FIG. 1 is a schematic flowchart of a method for generating a TMS coil pose atlas based on electromagnetic simulating calculation according to an embodiment of the present invention.

As shown in FIG. 1, a method for generating a TMS coil pose atlas based on electromagnetic simulating calculation in the present invention includes the following steps:

Step S10: Construct coil array positions and orientations of a scalp in a standard MNI space and match the coil array positions and orientations of the scalp to a brain space of an individual to obtain coil array positions and orientations of the brain space of the individual.

Step S20: Construct a finite element model for the electromagnetic simulating calculation based on obtained structural magnetic resonance images and diffusion tensor magnetic resonance images of a brain of the individual, use a finite element calculation method to simulate the coil array positions of the brain space of the individual to obtain induced electric field distributions of brain tissue in different coil orientations.

Step S30: Register a brainnetome atlas of the standard space to the brain space of the individual to obtain a brain area division result of the individual, and obtain a first electric field intensity and a second electric field intensity based on the induced electric field distributions of the brain tissue; and use a maximum value of a sum of the first electric field intensity and a ratio of the first electric field intensity to the second electric field intensity as an optimal regulation effect. The first electric field intensity is an average electric field intensity of an ROI. The second electric field intensity is an average electric field intensity of a region other than the ROI in each divided brain area, namely, an electric field intensity of a non-ROI. The ROI is a spherical region with a specified radius around a center of each divided brain area of the individual.

Step S40: Obtain a coil position and orientation corresponding to each optimal regulation effect as an optimal coil pose of each divided brain area of the individual; and construct a TMS coil pose atlas of the individual based on the optimal coil pose.

To describe the method more clearly for generating a TMS coil pose atlas based on electromagnetic simulating calculation in the present invention, the following describes in detail the steps in an embodiment of the method in the present invention with reference to the accompanying drawings.

Figure 3A:
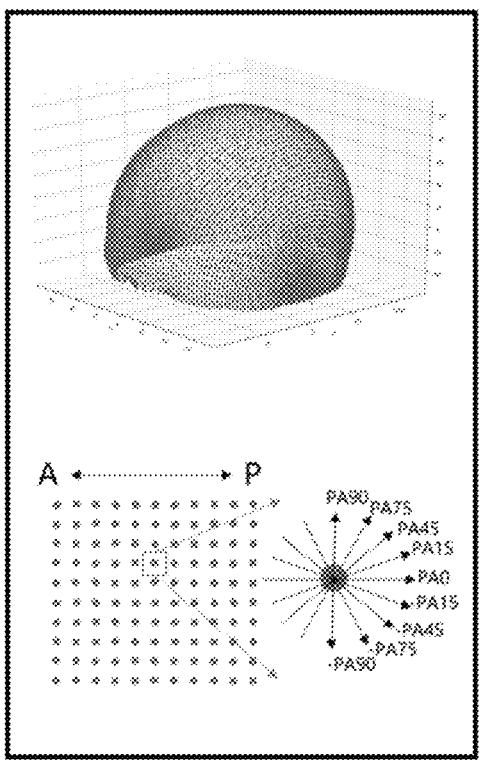
FIGS. 3A-3C are schematic diagrams of a simplified generation process of a TMS coil pose atlas according to an embodiment of the present invention.
Figure 3B:
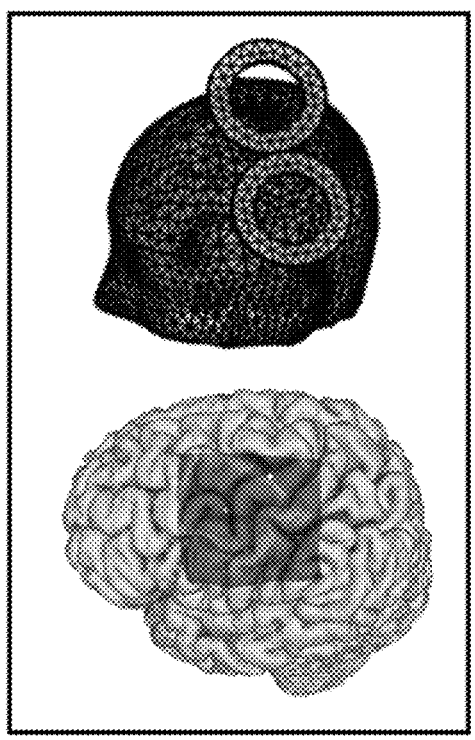
Figure 3C:
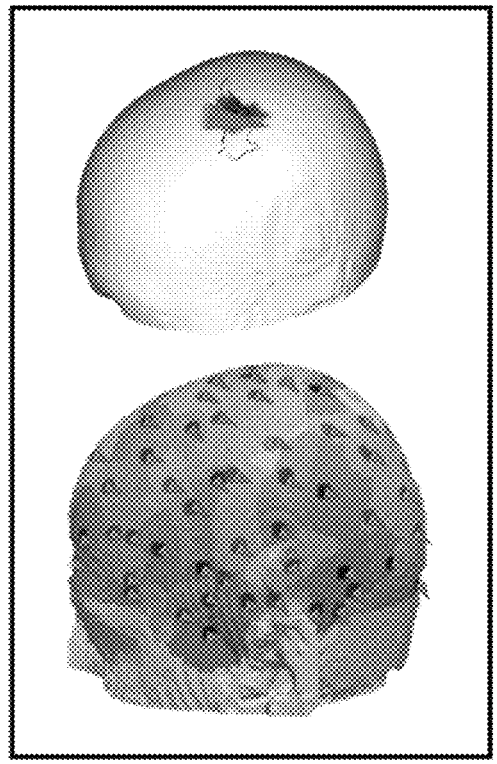

In the present invention, positions and orientations of a coil positioning array of a scalp in a standard MNI space are first constructed to implement quantitative description of coil positions on scalps of different participants. Then, a head finite element simulating calculation model of an anisotropic electrical parameter is established based on magnetic resonance images of the participants, and induced electric field distributions of brain tissue in different regulation states of combinations of the coil positioning array positions and orientations are sequentially calculated. Finally, correspondences between brain subregions in a brainnetome atlas and regulation effects are established based on the electric field distributions, and backward induction is performed to obtain optimal TMS coil poses based on corresponding target regulation areas and regulation effects, to form a new type of TMS coil pose atlas. As shown in FIGS. 3A-3C:

In FIG. 3A, the TMS coil array positions are constructed of the scalp and used as possible positioning positions of the coil. Each coil position is given a plurality of coil orientations, which are used as possible positioning orientations of the coil. A finite element calculation model of an anisotropic electrical parameter is constructed for a specific individual (such as the participant in FIG. 3B). Induced electric field distributions in the brain tissue of the individual for all coil positions and orientations are simulated and calculated. To achieve an optimal regulation effect and a minimum side effect, backward induction can be performed to obtain an optimal coil position and orientation corresponding to a specific target area at a group level. In FIG. 3C, after optimal coil positions and orientations are standardized to the standard brain space, probability correspondences between optimal regulation effects and coil poses can be obtained. Based on information about target regulation areas obtained from a given brain atlas, the probability correspondences can provide a group-level probability of a coil pose that enables each target brain area to achieve an optimal regulation effect, and the probability is used as prior knowledge. The TMS coil pose atlas is essentially prior knowledge of the coil pose that maps the optimal regulation effect of the scalp for the target regulation area. If only the probability of the optimal coil pose and regulation effect for the target area is considered, a maximum pose probability diagram shown in FIG. 3C can be used as a useful guide for coil positioning.

The TMS coil pose atlas can be used to directly obtain an optimal coil pose corresponding to a target regulation area based only on magnetic resonance images of a participant. In addition, the TMS coil pose atlas can use prior brain areas in the brain atlas as target areas and provide optimal coil positions and orientations based on the group-level correspondences between regulation effects and coil poses for the target areas. Under the framework of the TMS coil pose atlas, coil pose data is obtained based on the optimal regulation effect and minimum side effect calculated through group-level simulation. This can conveniently and quickly guide placement of a TMS coil on the participant's scalp. Therefore, the construction of the TMS coil pose atlas resolves a problem that coil positioning is isolated from regulation effects in TMS neuronavigation technologies.

A process of generating the TMS coil pose atlas includes the following steps:

Step S10: Construct coil array positions and orientations of a scalp in a standard MNI space and match the coil array positions and orientations of the scalp to a brain space of an individual to obtain coil array positions and orientations of the brain space of the individual.

The coil array position and orientation need to meet the following two basic requirements: First, a mapping of a target regulation brain area to the scalp is provided. Second, considering differences in anatomical structures of individuals in a group, different individuals, each coil array position of the scalp is basically the same neuroanatomically.

Figure 4A:
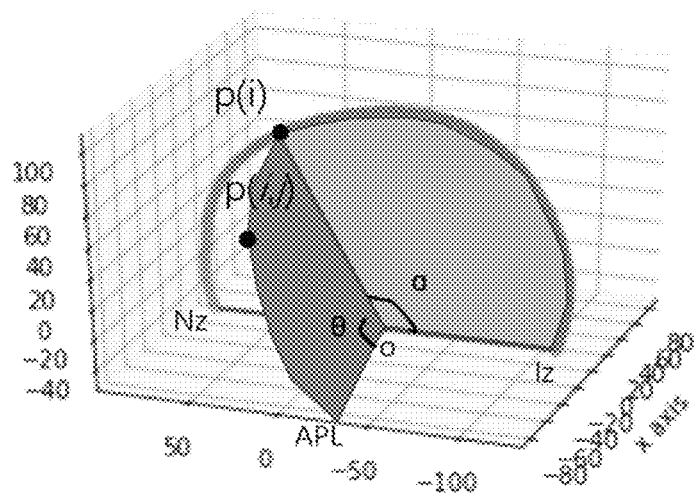
FIGS. 4A-4B are schematic diagrams of constructing a coil array position and orientation in standard MNI space according to an embodiment of the present invention.

The coil array positions are constructed based on an equiangular coordinate system. The basic idea is to divide the standard brain space to regions of equal angles. A point at which a radial line intersects the scalp is determined as a coil array position in the standard space. Then, the position is registered to the brain space of the individual to obtain a coil array pose of the brain space of the individual. In this embodiment, the coil array positions are constructed of the scalp in the standard space through the following steps, as shown in FIG. 4A:

Step S11: Mark anatomical reference points of the scalp in the standard MNI space.

In the present invention, there are at least three anatomical reference points. In this embodiment, four anatomical reference points are preferred, including a nasion Nz, an occipital protuberance Iz, a front vertex of a right external pinna APR, and a front vertex of a left external pinna APL. The standard MNI space preferably uses a standard MNI 152 template in the present invention.

Step S12: Obtain a curve l1 for connecting Nz and Iz and a curve l2 for connecting APR and APL, determine an intersection point of l1 and l2 as a central point Cz, and project Cz onto a plane on which Nz and APR are located to obtain a point O; and establish an equiangular coordinate system based on O, Cz, Nz, and APR, where O is an origin of the coordinate system, Nz is in a positive orientation of an x-axis of the coordinate system, APR is in a positive orientation of a y-axis of the coordinate system, and Cz is in a positive orientation of a z-axis of the coordinate system.

Step S13: Connect Nz, Cz, Iz, and O sequentially, divide an Nz-O-Iz angle into M equal angles α, and determine a point at which a radial line in each orientation intersects the scalp as p(i), where p(1) represents Nz, p(M+1) represents Iz, and M is a positive integer.

Step S14: For each point p(i), connect APL, p(i), APR, and O sequentially, divide an included angle into M equal angles θ, and determine a point at which a radial line in each orientation intersects the scalp to be p(i, j) as a coil array position of the scalp in the standard MNI space, where p(i, 1) represents APL, and p(i, M+1) represents APR.

Figure 4B:
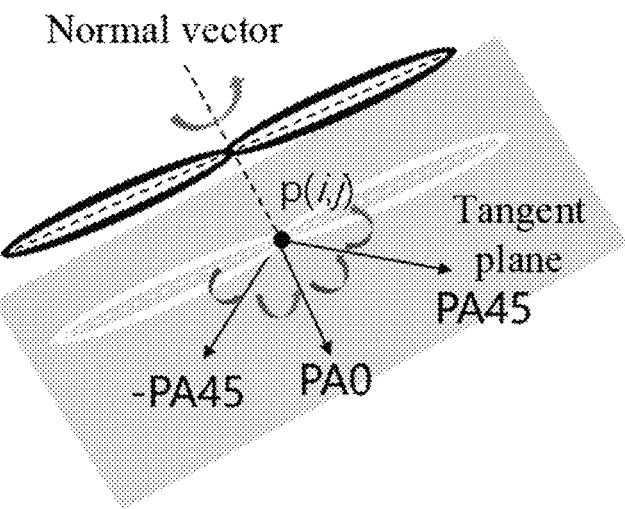

The coil array position p(i, j) in the standard MNI space is obtained by performing the foregoing steps, and then the standard space is registered to the brain space of the individual to obtain the coil array position of the brain space of the individual. To construct coil orientations, first determine a normal vector and a tangent plane of the array point p(i, j) of the scalp, and then determine an orientation parallel to a posterior-to-anterior orientation PA in a medical image as PA0. A process of determining the coil orientations includes: rotating a coil center around the normal vector by a specific angle on the tangent plane, as shown in FIG. 3A and FIG. 4B. The specific process of constructing the coil orientations is as follows:

For each coil array position, fit a curved surface of the coil array position and surrounding coil array positions, solve a normal line of the array position on the curved surface toward the outside of the scalp, and solve a tangent plane passing through the position and perpendicular to the normal line based on the normal line of the array position.

Define a posterior-to-anterior orientation on a sagittal plane in a medical imaging space as a 0-degree orientation, and translate the 0-degree orientation to a specific coil array position to locate the 0-degree orientation of the position. a PA orientation with the position as an origin and toward the sagittal plane is expressed as PA0. Angles of other orientations on the coil tangent plane can be set based on PA0.

Step S20: Construct a finite element model for the electromagnetic simulating calculation based on obtained structural magnetic resonance images and diffusion tensor magnetic resonance images of a brain of the individual, use a finite element calculation method to simulate the coil array positions of the brain space of the individual to obtain induced electric field distributions of brain tissue in different coil orientations.

In this embodiment, a process of constructing the finite element model for the electromagnetic simulating calculation is as follows:

Step S21: Obtain an electrical conductivity parameter of each brain tissue of the brain space of the individual based on the obtained structural magnetic resonance images of the brain of the individual, divide the brain space into N parts based on a threshold of the electrical conductivity parameter, and perform three-dimensional reconstruction to obtain a finite element geometric model.

Figure 5A:
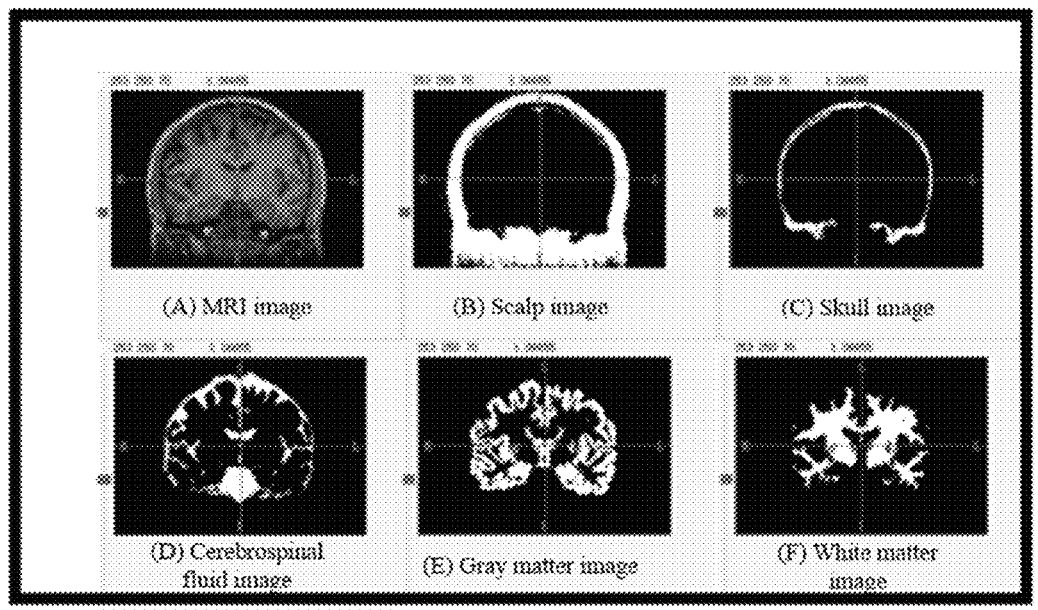
FIGS. 5A-5D are schematic diagrams of calculating induced electric field distributions by using a finite element model according to an embodiment of the present invention.
Figure 5B:
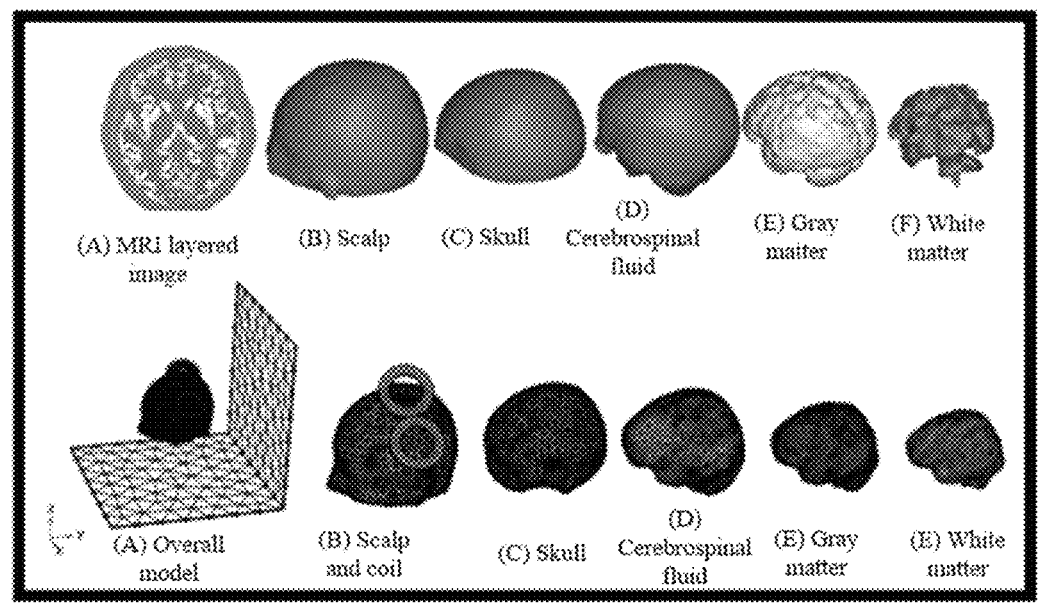

In this embodiment, N is preferably set to 5. To be specific, the brain space is divided into the scalp, skull, cerebrospinal fluid, gray matter, and white matter (as shown in FIG. 5A). Three-dimensional reconstruction is performed to obtain the finite element geometric model (as shown in FIG. 5B). The structural magnetic resonance images include T1 and T2 structural magnetic resonance images. T1 uses a selective water excitation method for scanning and can suppress fat and spongy bone signals of the skull. T2 uses a high read bandwidth method for scanning and can reduce fat deviation and separate the scalp, skull, and cerebrospinal fluid.

Step S22: Calculate a diffusion tensor matrix and an eigenvalue and an eigenvector of the diffusion tensor matrix based on the obtained diffusion tensor magnetic resonance images of the individual; and construct an anisotropic electrical parameter of the brain tissue based on an inference that an eigenvalue of an electrical conductivity tensor matrix of a volume constraint model is proportional to an eigenvalue of the diffusion tensor matrix, and an eigenvector of the electrical conductivity tensor matrix is identical to an eigenvector of the diffusion tensor matrix.

Figure 5C:
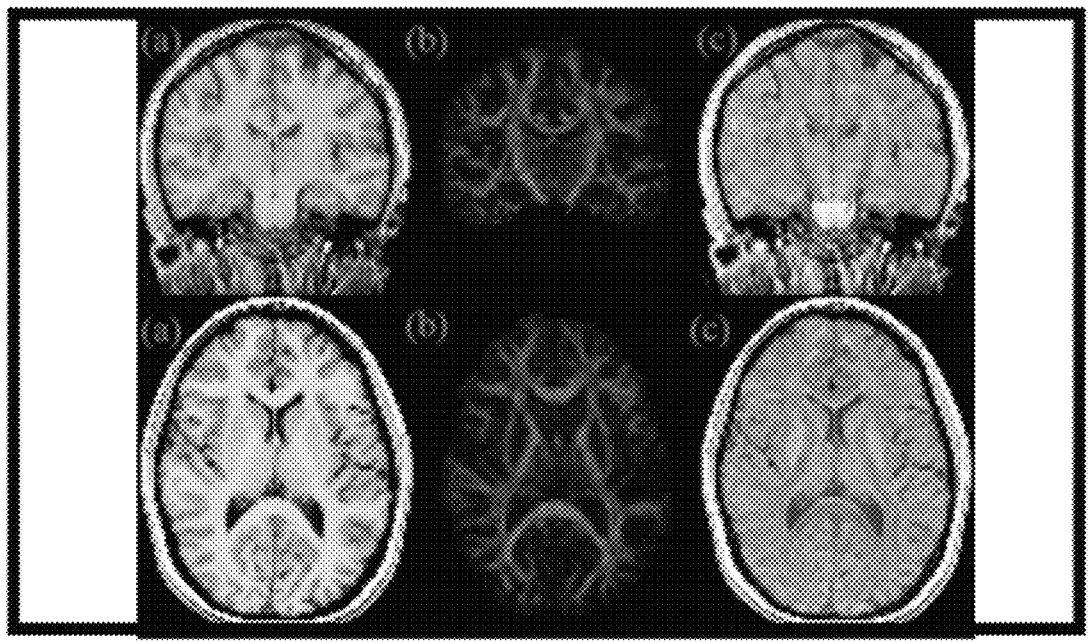

In this embodiment, the diffusion tensor magnetic resonance images include diffusion tensor magnetic resonance images in anterior-posterior and posterior-to-anterior orientations. The diffusion tensor matrix and an eigenvalue and an eigenvector of the diffusion tensor matrix are calculated based on diffusion magnetic resonance imaging data. The anisotropic electrical parameter (as shown in FIG. 5C) of the brain tissue is constructed based on the inference that the eigenvalue of the electrical conductivity tensor matrix of the volume constraint model is approximately proportional to an eigenvalue of the diffusion tensor matrix, and an eigenvector of the electrical conductivity tensor matrix is identical to an eigenvector of the diffusion tensor matrix. The volume constraint model is expressed as formula (1).

$$\frac{4}{3}\pi(\sigma_{iso})^3 = \frac{4}{3}\pi(\sigma_1 \sigma_2 \ldots \ldots \sigma_i) \quad (1)$$

where $\sigma_{iso}$ represents an isotropic electrical conductivity parameter of the brain tissue (in the present invention, a preferred value of $\sigma_{iso}$ is determined by using a Cole-Cole model), and $\sigma_i$ (in the present invention, i is preferably set to 3) represents the eigenvalue of the electrical conductivity tensor matrix, indicating that an anisotropic conductive ellipsoid has the same volume as an isotropic conductive ellipsoid. In addition, the eigenvalue of the electrical conductivity tensor matrix is proportional to the eigenvalue of the diffusion tensor matrix, as expressed by formula (2).

$$\frac{d_1}{\sigma_1} = \frac{d_2}{\sigma_2} = \frac{d_3}{\sigma_3} \quad (2)$$

where $d_i$ (i=1, 2, 3) represents the eigenvalue of the diffusion tensor matrix.

Because the eigenvector of the electrical conductivity tensor matrix is identical to the eigenvector of the diffusion tensor matrix, the electrical conductivity tensor matrix $\Sigma$ can be obtained in combination with the eigenvalue of the electrical conductivity tensor matrix, as expressed by formula (3).

$$\sum = \begin{pmatrix} \sigma_{xx} & \sigma_{xy} & \sigma_{xz} \\ \sigma_{yx} & \sigma_{yy} & \sigma_{yz} \\ \sigma_{zx} & \sigma_{zy} & \sigma_{zz} \end{pmatrix} = V \cdot \begin{pmatrix} \sigma_1 & 0 & 0 \\ 0 & \sigma_2 & 0 \\ 0 & 0 & \sigma_3 \end{pmatrix} \cdot V' \quad (3)$$

Step S23: Construct the finite element model for the electromagnetic simulating calculation of the individual based on the finite element geometric model and the anisotropic electrical parameter of the brain tissue, and use the finite element calculation method to simulate positioning of a TMS coil at the coil array positions of the brain space of the individual to obtain the induced electric field distributions of the brain tissue at the coil array positions of the brain space of the individual and in different coil orientations.

In this embodiment, the induced electric field E distribution in the finite element electromagnetic simulation is solved according to the Helmholtz theorem, and is composed of two parts:

$$-\frac{\partial A}{\partial t}$$

generated by pulse current and $-\nabla\Phi$ generated by charge distribution, as expressed by formula (4).

$$E = -\frac{\partial A}{\partial t} - \nabla\Phi$$

A magnetic vector potential A can be solved according to the Biot-Savart law. According to the Biot-Savart law, the magnetic vector potential A is related to the position of the TMS coil, a geometric structure of the brain tissue, and the electrical conductivity parameter of the brain tissue. A scalar potential $\Phi$ can be obtained by solving a Laplace equation according to the Neummn boundary condition. The scalar potential is affected by the distribution of the brain tissue, the electrical conductivity parameter, and the position of the stimulation coil.

Figure 5D:
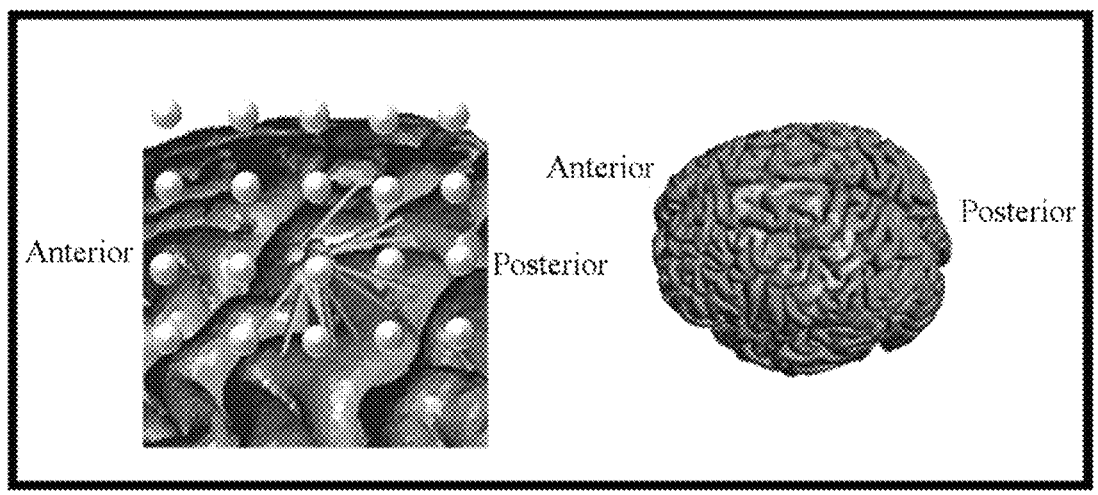

The coil used in the TMS scheme of the present invention is a figure-eight coil with an outer diameter of 9.7 cm and an inner diameter of 4.7 cm. Stimulation current of all the simulated and calculated coil is 1 A. The induced electric field distributions of the head corresponding to all coil array poses and coil orientations are calculated, as shown in FIG. 5D.

Step S30: Register a brainnetome atlas of the standard space to the brain space of the individual to obtain a brain area division result of the individual, and obtain a first electric field intensity and a second electric field intensity based on the induced electric field distributions of the brain tissue; and use a maximum value of a sum of the first electric field intensity and a ratio of the first electric field intensity to the second electric field intensity as an optimal regulation effect. The first electric field intensity is an average electric field intensity of an ROI. The second electric field intensity is an average electric field intensity of a region other than the ROI in each divided brain area, namely, an electric field intensity of a non-ROI. The ROI is a spherical region with a specified radius around a center of each divided brain area of the individual.

In this embodiment, the brain atlas of the standard space is registered to the brain space of the individual to construct the brain atlas of the individual and obtain the brain area division result of the individual.

Figure 6A:
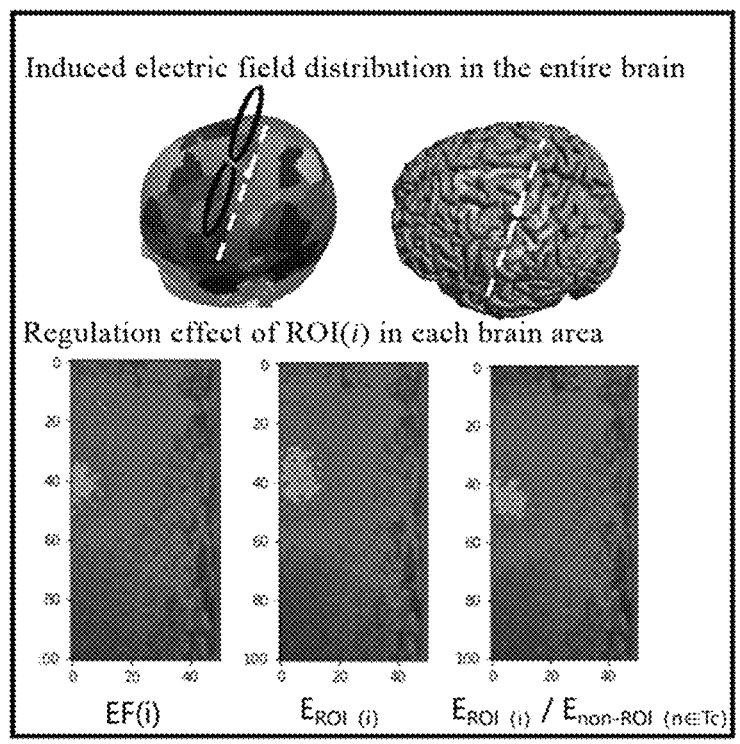
FIGS. 6A-6B are schematic diagrams of constructing a TMS coil pose atlas based on a correspondence between an optimal regulation effect and a coil pose according to an embodiment of the present invention.

A sphere with a specified radius is constructed with the center of each divided brain area in the brainnetome atlas of the individual as the center, and is an ROI for each regulation brain area. The radius is preferably set to 3 mm. In this embodiment of the present invention, the optimal regulation effect is defined as a maximum induced electric field intensity of ROI(i) in each divided brain area and a minimum induced electric field intensity of the non-ROI. Therefore, the regulation effect EF(i) can be quantitatively described and is calculated by using formula (5).

$$EF(i) = E_{ROI(i)} + \frac{E_{ROI(i)}}{E_{non-ROI(n \in Tc)}} \quad (5)$$

where EF(i) represents a regulation effect, namely, an induced electric field intensity, $E_{ROI(i)}$ represents an average induced electric field intensity of an $i^{th}$ ROI, and $E_{non-ROI(n \in Tc)}$ represents an average induced electric field intensity of a region other than the $i^{th}$ ROI in a current divided brain area (as shown in FIG. 6A).

In the present invention, the maximum regulation effect EF(i) of ROI(i) in each divided brain area is calculated and saved as [s] (which consists of k coil array poses and m coil orientations), as expressed by formulas (6) and (7).

$$EF_{max}(i) = \max_{k \times m \in [s]} |EF(P_{k(i)}, O_{m(i)})| \quad (6)$$

$$(P_{opt}(i), O_{opt}(i)) = \arg\max_{k \times m \in [s]} |EF(P_{k(i)}, O_{m(i)})| \quad (7)$$

where $P_{k(i)}$ represents a coil position corresponding to the $i^{th}$ ROI, $O_{m(i)}$ represents a coil orientation corresponding to the $i^{th}$ ROI, k represents a number of coil positions, m represents a number of coil orientations, $P_{opt}(i)$ represents a coil position corresponding to the maximum regulation effect of the $i^{th}$ ROI, and $O_{opt}(i)$ represents the coil orientation corresponding to the maximum regulation effect of the $i^{th}$ ROI.

Step S40: Obtain a coil position and orientation corresponding to each optimal regulation effect as an optimal coil pose of each divided brain area of the individual; and construct a TMS coil pose atlas of the individual based on the optimal coil pose.

Figure 6B:
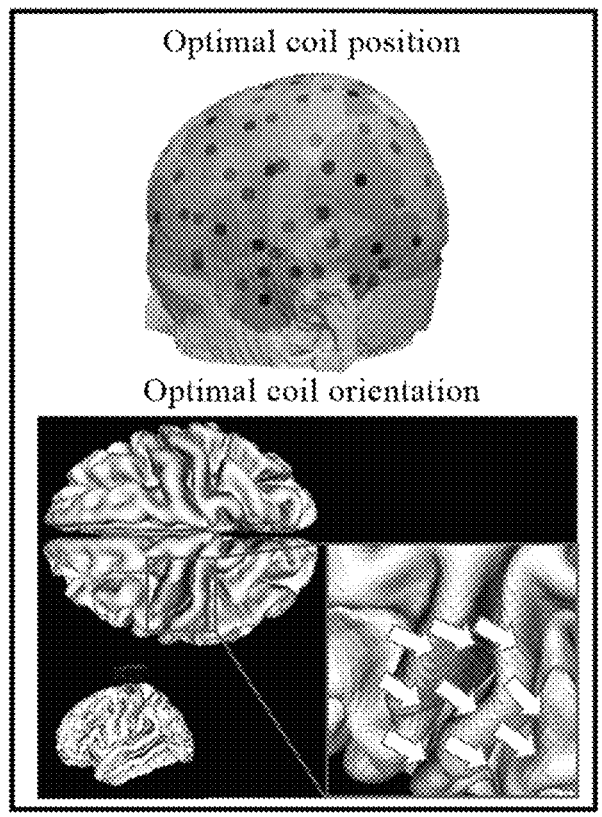

In this embodiment, the coil position and orientation corresponding to each optimal regulation effect are obtained as the optimal coil pose of each divided brain area of the individual, as shown in FIG. 6B. The TMS coil pose atlas of the individual is constructed based on the optimal coil pose.

In addition, the optimal coil poses of all brain areas of the individual can be obtained through the foregoing steps. However, there are obvious individual differences in the brain structure and head geometry of different individuals. The foregoing optimal coil poses calculated by using the finite element model of the individual cannot be directly applied to a group. Therefore, it is necessary to include as many common features of the group as possible and reduce individual differences. In view of this, in an embodiment of the present invention, a magnetic resonance imaging dataset of 16 participants is used to provide an example of constructing a TMS coil pose atlas based on a brainnetome atlas. The following describes a process of generating a group-level TMS coil pose atlas.

The magnetic resonance imaging dataset of 16 healthy participants in a Human Connectome Project (HCP) database is used. The standard brain space is registered to the brain space of the individual to obtain the coil array positions of the brain space of the individual. All coil poses ($P_k$, $O_m$) of the scalp of the individual can be obtained by using the method for determining coil orientations in the present invention.

To simulate and calculate induced electric field distributions, finite element simulating calculation software needs to be used to construct an anisotropic finite element model of the individual, and calculate induced electric field distributions in all coil pose states. In an embodiment of the present invention, Simulated Time Series B (SIMNSB) software is used to construct the finite element model and calculate the induced electric field distributions.

The regulation effect of ROI(i) in the brain area is standardized into Z based on the induced electric field distributions in all coil pose states, and first-order smoothing is performed on a Z value for each participants. Then, an average of Z values for the participants is calculated to obtain an average Z value for the group. Areas whose Z value is greater than 0.05 are selected as significant areas. Poses corresponding to top 30 largest Z values are selected for each divided brain area to construct the group-level TMS coil pose atlas.

In this embodiment of the present invention, the TMS coil pose atlas is constructed based on the brainnetome atlas with 246 brain subregions. The brain subregions are projected onto the scalp in the standard space by using a shortest distance method. Each subregion is represented by a different color. The figure shows a boundary shape of the subregion. The TMS coil pose atlas is constructed based on the brain subregion distribution atlas of the scalp. Darker dots indicate group-level coil positions, and triangles indicate coil orientations corresponding to each coil position, as shown in FIG. 3C. The triangle in the figure represents an average horizontal group-level coil orientation. A base length of the triangle represents a range of the group-level coil orientation. In addition, TMS cannot be applied to subregions such as a nucleus located in a deep part of the brain. Therefore, such brain subregions are ignored in this embodiment of the present invention.

Figure 2:
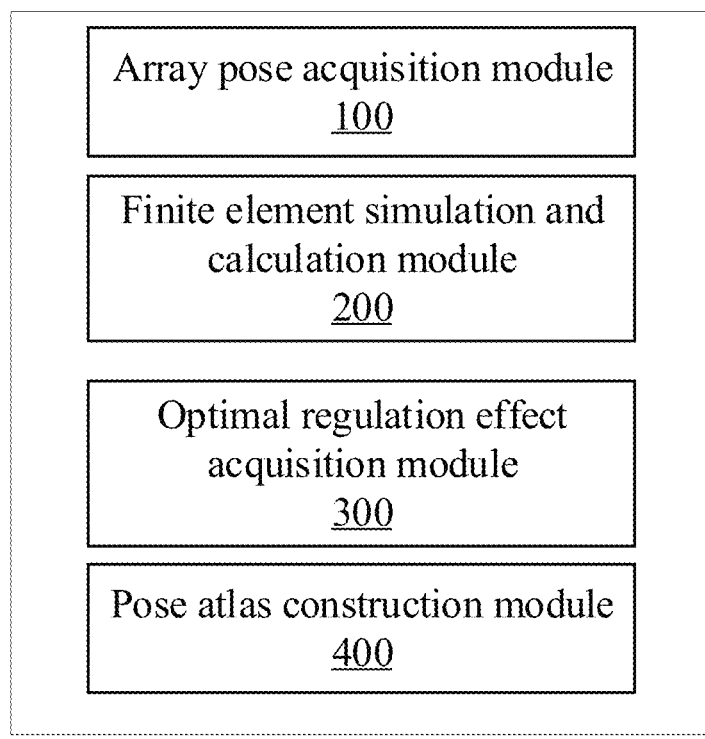
FIG. 2 is a schematic diagram of a system for generating a TMS coil pose atlas based on electromagnetic simulating calculation according to an embodiment of the present invention.

In a second embodiment of the present invention, a system for generating a TMS coil pose atlas based on electromagnetic simulating calculation is provided. As shown in FIG. 2, the system specifically includes an array pose acquisition module 100, a finite element simulating calculation module 200, an optimal regulation effect acquisition module 300, and a pose atlas construction module 400.

The array pose acquisition module 100 is configured to construct coil array positions and orientations of a scalp in a standard MNI space and match the coil array positions and orientations of the scalp to a brain space of an individual to obtain coil array positions and orientations of the brain space of the individual.

The finite element simulating calculation module 200 is configured to construct a finite element model for the electromagnetic simulating calculation based on obtained structural magnetic resonance images and diffusion tensor magnetic resonance images of a brain of the individual, use a finite element calculation method to simulate the coil array positions of the brain space of the individual to obtain induced electric field distributions of brain tissue in different coil orientations.

The optimal regulation effect acquisition module 300 is configured to register a brainnetome atlas of the standard space to the brain space of the individual to obtain a brain area division result of the individual, and obtain a first electric field intensity and a second electric field intensity based on the induced electric field distributions of the brain tissue; and use a maximum value of a sum of the first electric field intensity and a ratio of the first electric field intensity to the second electric field intensity as an optimal regulation effect. The first electric field intensity is an average electric field intensity of an ROI. The second electric field intensity is an average electric field intensity of a region other than the ROI in each divided brain area, namely, an electric field intensity of a non-ROI. The ROI is a spherical region with a specified radius around a center of each divided brain area of the individual.

The pose atlas construction module 400 is configured to obtain a coil position and orientation corresponding to each optimal regulation effect as an optimal coil pose of each divided brain area of the individual; and construct a TMS coil pose atlas of the individual based on the optimal coil pose.

Those skilled in the art can clearly understand that, for convenience and brevity of description, reference can be made to corresponding processes in the foregoing method embodiments for a specific working process and a related description of the foregoing system. Details are not described herein again.

It should be noted that the system for generating a TMS coil pose atlas based on electromagnetic simulating calculation provided in the foregoing embodiment is illustrated only based on division of the foregoing functional modules. In practical application, the foregoing functions may be completed by different functional modules according to needs. That is, the modules or steps in the embodiments of the present invention can be decomposed or combined again, for example, the modules of the foregoing embodiments can be combined into one module or further divided into a plurality of sub-modules to complete all or some of the functions described above. The names of the modules and steps involved in the embodiments of the present invention are only for distinguishing each module or step, and should not be regarded as improper limitations on the present invention.

In a third embodiment of the present invention, a device is provided. The device includes at least one processor and a memory communicatively connected to the at least one processor. The memory stores an instruction executable by the processor. The instruction is configured to be executed by the processor to implement the foregoing method for generating a TMS coil pose atlas based on electromagnetic simulating calculation.

A fourth embodiment of the present invention provides a computer-readable storage medium. The computer-readable storage medium stores a computer instruction. The computer instruction is configured to be executed by a computer to implement the foregoing method for generating a TMS coil pose atlas based on electromagnetic simulating calculation.

Those skilled in the art can clearly understand that, for convenience and brevity of description, reference can be made to a corresponding process in the foregoing method embodiments for specific working processes and related descriptions of the foregoing storage apparatus and processing apparatus. Details are not described herein again.

It should be noted that, the computer-readable medium in the present invention may be a computer-readable signal medium, a computer-readable storage medium, or a combination thereof. The computer-readable storage medium may be, for example, but not limited to, an electrical, magnetic, optical, electromagnetic, infrared, or semiconductor system, apparatus, or device, or any combination thereof. More specific examples of the computer-readable storage medium may include, but is not limited to an electrical connection with one or more conducting wires, a portable computer disk, a hard disk, a random access memory (RAM), a read-only memory (ROM), an erasable programmable ROM (EPROM) or a flash memory, an optical fiber, a portable compact disk ROM (CD-ROM), an optical storage device, a magnetic storage device, or any suitable combination thereof. In the present invention, the computer-readable storage medium may be any tangible medium including or storing a program. The program may be used by or used in combination with an instruction execution system, apparatus, or device. In the present invention, the computer-readable signal medium may include a data signal propagated in a baseband or propagated as a part of a carrier, and carries computer-readable program code. The propagated data signal may be in various forms, including but not limited to an electromagnetic signal, an optical signal, or any suitable combination thereof. The computer-readable signal medium may alternatively be any computer-readable medium except the computer-readable storage medium. The computer-readable medium may send, propagate, or transmit a program used by or used in combination with an instruction execution system, apparatus, or device. The program code contained on the computer readable medium may be transmitted by using any suitable medium, including but not limited to the following: wireless, wire, optical fiber, radio frequency, or any suitable combination thereof.

The computer program code for executing the operations in the present invention may be compiled by using one or more program design languages or a combination thereof. The programming languages include object-oriented programming languages, such as Java, Smalltalk, and C++, and conventional procedural programming languages, such as C or similar programming languages. The program code may be executed fully on a user computer, executed partially on a user computer, executed as an independent software package, executed partially on a user computer and partially on a remote computer, or executed fully on a remote computer or a server. Where the remote computer is involved, the remote computer may be connected to the user computer through any kind of network, including the local area network (LAN) or the wide area network (WAN), or may be connected to the external computer (for example, the remote computer is connected through the internet by an internet service provider).

The flowcharts and block diagrams in the accompanying drawings illustrate system architectures, functions, and operations that may be implemented by the system, method, and computer program product according to the embodiments of the present invention. In this regard, each block in the flowcharts or block diagrams may represent a module, a program segment or a part of code, and the module, the program segment or the part of code includes one or more executable instructions for implementing specified logic functions. It should also be noted that, in some alternative implementations, the functions marked in the blocks may alternatively occur in a different order from that marked in the accompanying drawings. For example, two successively shown blocks actually may be executed in parallel substantially, or may be executed in reverse order sometimes, depending on the functions involved. It should also be noted that each block in the flowcharts and/or block diagrams and combinations of the blocks in the flowcharts and/or block diagrams may be implemented by a dedicated hardware-based system for executing specified functions or operations, or may be implemented by a combination of dedicated hardware and computer instructions.

Terms such as "first" and "second" are intended to distinguish between similar objects, rather than describe or indicate a specific order or sequence.

Terms "include", "comprise", or any other variations thereof are intended to cover non-exclusive inclusions, so that a process, a method, an article, or a device/apparatus including a series of elements not only includes those elements, but also includes other elements that are not explicitly listed, or also includes inherent elements of the process, the method, the article or the device/apparatus.

The technical solutions of the present invention are described with reference to the preferred implementations and drawings. Those skilled in the art should easily understand that the protection scope of the present invention is apparently not limited to these specific implementations. Those skilled in the art can make equivalent changes or substitutions to the relevant technical features without departing from the principles of the present invention, and the technical solutions after these changes or substitutions should fall within the protection scope of the present invention.

What is claimed is:

1. A method for generating a transcranial magnetic stimulation (TMS) coil pose atlas based on an electromagnetic simulating calculation, comprising:

step S10: constructing, by at least one processor, coil array positions and orientations of a scalp in a standard Montreal Neurological Institute (MNI) space and matching the coil array positions and orientations of the scalp to a brain space of an individual to obtain coil array positions and orientations of the brain space of the individual, wherein the at least one processor is coupled to a memory storing instructions, and when the instructions are executed by the at least one processor, cause the at least one processor to perform the disclosed steps;

step S20: constructing, by the at least one processor, a finite element model for the electromagnetic simulating calculation based on obtained structural magnetic resonance images and diffusion tensor magnetic resonance images of a brain of the individual, using a finite element calculation method to simulate positioning of a TMS coil at the coil array positions of the brain space of the individual to obtain induced electric field distributions of brain tissue in different coil orientations;

wherein a method for obtaining the induced electric field distributions of the brain tissue in different coil orientations comprises:

obtaining an electrical conductivity parameter of each brain tissue of the brain space of the individual based on the structural magnetic resonance images, dividing the brain space into N parts based on a threshold of the electrical conductivity parameter, and performing three-dimensional reconstruction to obtain a finite element geometric model;

calculating a diffusion tensor matrix and an eigenvalue and an eigenvector of the diffusion tensor matrix based on the diffusion tensor magnetic resonance images; and constructing an anisotropic electrical parameter of the brain tissue based on an inference that an eigenvalue of an electrical conductivity tensor matrix of a volume constraint model is proportional to the eigenvalue of the diffusion tensor matrix, and an eigenvector of the electrical conductivity tensor matrix is identical to the eigenvector of the diffusion tensor matrix; and constructing the finite element model for the electromagnetic simulating calculation of the individual based on the finite element geometric model and the anisotropic electrical parameter of the brain tissue, and using the finite element calculation method to simulate the positioning of the TMS coil at the coil array positions of the brain space of the individual to obtain the induced electric field distributions of the brain tissue in different coil orientations;

wherein the volume constraint model is as follows:

$$\frac{4}{3}\pi(\sigma_{iso})^3 = \frac{4}{3}\pi(\sigma_1\sigma_2 \ldots \sigma_i)$$

wherein $\sigma_{iso}$ represents an isotropic electrical conductivity parameter of the brain tissue, and $\sigma_i$ represents the eigenvalue of the electrical conductivity tensor matrix;

step S30: registering, by the at least one processor, a brainnetome atlas of the standard MNI space to the brain space of the individual to obtain a brain area division result of the individual, and obtaining a first electric field intensity and a second electric field intensity based on the induced electric field distributions of the brain tissue; and using a maximum value of a sum of the first electric field intensity and a ratio of the first electric field intensity to the second electric field intensity as an optimal regulation effect, wherein the first electric field intensity is an average electric field intensity of a region of interest (ROI), the second electric field intensity is an average electric field intensity of a region other than the ROI in each divided brain area, namely, an electric field intensity of a non-ROI, and the ROI is a spherical region with a specified radius around a center of each divided brain area of the individual; and step S40: obtaining, by the at least one processor, a coil position and orientation corresponding to each optimal regulation effect as an optimal coil pose of each divided brain area of the individual; and constructing a TMS coil pose atlas of the individual based on the optimal coil pose.

2. The method for generating the TMS coil pose atlas based on the electromagnetic simulating calculation according to claim 1, wherein the step of constructing the coil array positions of the scalp in the standard MNI space comprises:

step S11: marking anatomical reference points of the scalp in the standard MNI space, wherein the anatomical reference points comprise a nasion Nz, an occipital protuberance Iz, a front vertex of a right external pinna APR, and a front vertex of a left external pinna APL;

step S12: obtaining a curve l1 for connecting the Nz and the Iz and a curve l2 for connecting the APR and the APL, determining an intersection point of the l1 and the l2 as a central point Cz, and projecting the Cz onto a plane on which the Nz and the APR are located to obtain a point O; and establishing an equiangular coordinate system based on the O, the Cz, the Nz, and the APR, where the O is an origin of the coordinate system, the Nz is in a positive orientation of an x-axis of the coordinate system, the APR is in a positive orientation of a y-axis of the coordinate system, and the Cz is in a positive orientation of a z-axis of the coordinate system;

step S13: connecting the Nz, the Cz, the Iz, and the O sequentially, dividing an Nz-O-Iz angle into M equal angles α, and determining a point at which a radial line in each orientation intersects the scalp as p(i), where p(1) represents the Nz, p(M+1) represents the Iz, and the M is a positive integer; and step S14: for each point p(i), connecting the APL, the p(i), the APR, and the O sequentially, dividing an included angle into M equal angles θ, and determining a point at which a radial line in each orientation intersects the scalp to be p(i, j) as a coil array position of the scalp in the standard MNI space, where p(i, 1) represents the APL, and p(i, M+1) represents the APR.

3. The method for generating the TMS coil pose atlas based on the electromagnetic simulating calculation according to claim 2, wherein a method for constructing the coil array orientations of the scalp in the standard MNI space comprises:

determining a normal vector and tangent plane of a coil array pose of the scalp in the standard MNI space; and defining a posterior-to-anterior (PA) orientation on a sagittal plane in a medical imaging space as a 0-degree orientation, and translating the 0-degree orientation to a specific coil array position to locate the 0-degree orientation of the position, wherein the PA orientation with the position as an origin and toward the sagittal plane is expressed as PA0, and angles of other orientations on the coil tangent plane are set based on the PA0.

4. The method for generating the TMS coil pose atlas based on the electromagnetic simulating calculation according to claim 1, wherein the optimal regulation effect is calculated by using the following formulas:

$$EF_{max}(i) = \max_{k \times m \in [s]} |EF(P_{k(i)}, O_{m(i)})|$$

$$EF(i) = E_{ROI(i)} + \frac{E_{ROI(i)}}{E_{non-ROI(n \in Tc)}}$$

where EF(i) represents a regulation effect, namely, an induced electric field intensity, $EF_{max}(i)$ represents the optimal regulation effect, $E_{ROI(i)}$ represents an average induced electric field intensity of an $i^{th}$ ROI, $E_{non-ROI(n \in Tc)}$ represents an average induced electric field intensity of a region other than the $i^{th}$ ROI in a current divided brain area, $P_{k(i)}$ represents a coil position corresponding to the $i^{th}$ ROI, $O_{m(i)}$ represents a coil orientation corresponding to the $i^{th}$ ROI, k represents a number of coil positions, and m represents a number of coil orientations.

5. A system for generating a transcranial magnetic stimulation (TMS) coil pose atlas based on electromagnetic simulating calculation, comprising:

at least one processor and a memory communicatively connected to the at least one processor, wherein the memory stores an instruction executable by the at least one processor, and the instruction is configured to be executed by the at least one processor to implement an array pose acquisition module, a finite element simulating calculation module, an optimal regulation effect acquisition module, and a pose atlas construction module; wherein the array pose acquisition module is configured to construct coil array positions and orientations of a scalp in a standard Montreal Neurological Institute (MNI) space and match the coil array positions and orientations of the scalp to a brain space of an individual to obtain coil array positions and orientations of the brain space of the individual;

the finite element simulating calculation module is configured to construct a finite element model for the electromagnetic simulating calculation based on obtained structural magnetic resonance images and diffusion tensor magnetic resonance images of a brain of the individual, use a finite element calculation method to simulate the coil array positions of the brain space of the individual to obtain induced electric field distributions of brain tissue in different coil orientations;

wherein a method for obtaining the induced electric field distributions of the brain tissue in different coil orientations comprises:

obtaining an electrical conductivity parameter of each brain tissue of the brain space of the individual based on the structural magnetic resonance images, dividing the brain space into N parts based on a threshold of the electrical conductivity parameter, and performing three-dimensional reconstruction to obtain a finite element geometric model;

calculating a diffusion tensor matrix and an eigenvalue and an eigenvector of the diffusion tensor matrix based on the diffusion tensor magnetic resonance images; and constructing an anisotropic electrical parameter of the brain tissue based on an inference that an eigenvalue of an electrical conductivity tensor matrix of a volume constraint model is proportional to the eigenvalue of the diffusion tensor matrix, and an eigenvector of the electrical conductivity tensor matrix is identical to the eigenvector of the diffusion tensor matrix; and constructing the finite element model for the electromagnetic simulating calculation of the individual based on the finite element geometric model and the anisotropic electrical parameter of the brain tissue, and using the finite element calculation method to simulate the positioning of the TMS coil at the coil array positions of the brain space of the individual to obtain the induced electric field distributions of the brain tissue in different coil orientations;

wherein the volume constraint model is as follows:

$$\frac{4}{3}\pi(\sigma_{iso})^3 = \frac{4}{3}\pi(\sigma_1 \sigma_2 \ldots \sigma_i)$$

wherein $\sigma_{iso}$ represents an isotropic electrical conductivity parameter of the brain tissue, and $\sigma_i$ represents the eigenvalue of the electrical conductivity tensor matrix;

the optimal regulation effect acquisition module is configured to register a brainnetome atlas of the standard MNI space to the brain space of the individual to obtain a brain area division result of the individual, and obtain a first electric field intensity and a second electric field intensity based on the induced electric field distributions of the brain tissue; and use a maximum value of a sum of the first electric field intensity and a ratio of the first electric field intensity to the second electric field intensity as an optimal regulation effect, wherein the first electric field intensity is an average electric field intensity of a region of interest (ROI), the second electric field intensity is an average electric field intensity of a region other than the ROI in each divided brain area, namely, an electric field intensity of a non-ROI, and the ROI is a spherical region with a specified radius around a center of each divided brain area of the individual; and the pose atlas construction module is configured to obtain a coil position and orientation corresponding to each optimal regulation effect as an optimal coil pose of each divided brain area of the individual; and construct a TMS coil pose atlas of the individual based on the optimal coil pose.

6. A non-transitory computer-readable storage medium storing a computer instruction, and the computer instruction is configured to be executed by a computer processor to implement the method for generating the TMS coil pose atlas based on the electromagnetic simulating calculation according to claim 1.

7. The non-transitory computer-readable storage medium according to claim 6, wherein the step of constructing the coil array positions of the scalp in the standard MNI space comprises:

step S11: marking anatomical reference points of the scalp in the standard MNI space, wherein the anatomical reference points comprise a nasion Nz, an occipital protuberance Iz, a front vertex of a right external pinna APR, and a front vertex of a left external pinna APL;

step S12: obtaining a curve l1 for connecting the Nz and the Iz and a curve l2 for connecting the APR and the APL, determining an intersection point of the l1 and the l2 as a central point Cz, and projecting the Cz onto a plane on which the Nz and the APR are located to obtain a point O; and establishing an equiangular coordinate system based on the O, the Cz, the Nz, and the APR, where the O is an origin of the coordinate system, the Nz is in a positive orientation of an x-axis of the coordinate system, the APR is in a positive orientation of a y-axis of the coordinate system, and the Cz is in a positive orientation of a z-axis of the coordinate system;

step S13: connecting the Nz, the Cz, the Iz, and the O sequentially, dividing an Nz-O-Iz angle into M equal angles α, and determining a point at which a radial line in each orientation intersects the scalp as p(i), where p(1) represents the Nz, p(M+1) represents the Iz, and the M is a positive integer; and step S14: for each point p(i), connecting the APL, the p(i), the APR, and the O sequentially, dividing an included angle into M equal angles θ, and determining a point at which a radial line in each orientation intersects the scalp to be p(i, j) as a coil array position of the scalp in the standard MNI space, where p(i, 1) represents the APL, and p(i, M+1) represents the APR.

8. The non-transitory computer-readable storage medium according to claim 7, wherein a method for constructing the coil array orientations of the scalp m the standard MNI space comprises:

determining a normal vector and tangent plane of a coil array pose of the scalp in the standard MNI space; and defining a posterior-to-anterior (PA) orientation on a sagittal plane in a medical imaging space as a 0-degree orientation, and translating the 0-degree orientation to a specific coil array position to locate the 0-degree orientation of the position, wherein the PA orientation with the position as an origin and toward the sagittal plane is expressed as PA0, and angles of other orientations on the coil tangent plane are set based on the PA0.

9. The non-transitory computer-readable storage medium according to claim 6, wherein the optimal regulation effect is calculated by using the following formulas:

$$EF_{max}(i) = \max_{k \times m \in [s]} |EF(P_{k(i)}, O_{m(i)})|$$

$$EF(i) = E_{ROI(i)} + \frac{E_{ROI(i)}}{E_{non-ROI(n \in Tc)}}$$

where EF(i) represents a regulation effect, namely, an induced electric field intensity, $EF_{max}(i)$ represents the optimal regulation effect, $E_{ROI(i)}$ represents an average induced electric field intensity of an $i^{th}$ ROI, $E_{non-ROI(n \in Tc)}$ represents an average induced electric field intensity of a region other than the $i^{th}$ ROI in a current divided brain area, $P_{k(i)}$ represents a coil position corresponding to the $i^{th}$ ROI, $O_{m(i)}$ represents a coil orientation corresponding to the $i^{th}$ ROI, k represents a number of coil positions, and m represents a number of coil orientations.

* * * * *